(12) United States Patent
Munger et al.

(10) Patent No.: US 9,957,453 B2
(45) Date of Patent: May 1, 2018

(54) ENZYMATIC HYDROLYSIS OF ACYLATED STERYL GLYCOSIDES AND METHOD FOR TREATING BIOFUEL

(71) Applicant: ETH Zurich, Zurich (CH)

(72) Inventors: Linda Munger, Bern (CH); Laura Nystrom, Zurich (CH)

(73) Assignee: ETH Zurich, Zurich (CH)

( * ) Notice: Subject to any disclaimer, the term of this patent is extended or adjusted under 35 U.S.C. 154(b) by 69 days.

(21) Appl. No.: 14/912,127

(22) PCT Filed: Aug. 13, 2014

(86) PCT No.: PCT/EP2014/067336
§ 371 (c)(1),
(2) Date: Feb. 15, 2016

(87) PCT Pub. No.: WO2015/022367
PCT Pub. Date: Feb. 19, 2015

(65) Prior Publication Data
US 2016/0200992 A1    Jul. 14, 2016

(30) Foreign Application Priority Data

Aug. 16, 2013 (EP) .................................... 13004067

(51) Int. Cl.
| | | |
|---|---|---|
| *C12P 33/00* | (2006.01) | |
| *C10L 1/04* | (2006.01) | |
| *C11B 3/00* | (2006.01) | |
| *C12P 7/64* | (2006.01) | |

(52) U.S. Cl.
CPC ............... *C10L 1/04* (2013.01); *C11B 3/003* (2013.01); *C12P 7/6445* (2013.01); *C12P 33/00* (2013.01); *C10L 2200/0469* (2013.01); *C10L 2290/26* (2013.01)

(58) Field of Classification Search
CPC .. C10L 1/04; C10L 2200/469; C10L 2290/26; C11B 3/0003; C12P 33/00; C12P 7/6445
See application file for complete search history.

(56) References Cited

U.S. PATENT DOCUMENTS

| | | |
|---|---|---|
| 2005/0130281 A1 | 6/2005 | Both et al. |
| 2011/0099889 A1 | 5/2011 | Sohling et al. |
| 2011/0173876 A1 | 7/2011 | Soe |
| 2012/0009659 A1 | 1/2012 | Brask et al. |

FOREIGN PATENT DOCUMENTS

| | | |
|---|---|---|
| EP | 1531182 A2 | 5/2005 |
| EP | 2098585 A1 | 9/2009 |
| WO | 2009106360 A2 | 9/2009 |
| WO | 2010004423 A2 | 1/2010 |
| WO | 2010102952 A1 | 9/2010 |

OTHER PUBLICATIONS

Banik et al. Biotechnol. Bioprocess Engineer. (2012) 17: 925-936.*
"Enzyme Nomenclature" prepared by Edwin C. Webb (1992) (Academic Press, Inc.: SanDiego), p. 357.*
Kalinowska et al., "Purification and Some Properties of Steryl Beta-D-Glucoside Hydrolase from Sinapis Alba Seedlings," Phytochemistry, 1978, pp. 1533-1537, vol. 17, No. 9.
Kesselmeier et al., "High Performance Liquid Chromatography of Molecular Species from Free Sterols and Sterylglycosides Isolated from Oat Leaves and Seeds," Plant Cell Physiology, 1985, pp. 463-471, vol. 26, No. 3.
Strobl, "Δ7-Sterole und Δ7-Sterolglykoside aus Samen von *Cucurbita pepo* L.: Isolierung und Strukturaufklärung," Doctoral dissertation, Ludwig-Maximilians-Universität München, 2004.
Nystroem et al., "Enzymatic hydrolysis of steryl ferulates and steryl glycosides", European Food Research and Technology, 2007, vol. 227, No. 3, pp. 727-733.
Nystroem et al., "Steryl glycosides and acylated steryl glycosides in plant foods reflect unique sterol patterns", European Journal of Lipid Science and Technology, 2012, vol. 114, No. 6, pp. 656-669.

* cited by examiner

*Primary Examiner* — Susan M Hanley
(74) *Attorney, Agent, or Firm* — The Webb Law Firm

(57) ABSTRACT

The present invention relates to the use of at least one glycosidase of the class EC 3.2.1.21, EC 3.2.1.4, EC 3.2.1.7, and/or EC 3.2.1.80 for hydrolyzing at least one glycosiding bond in at least one substrate selected from the group of acylated steryl glycosides of the general formula (I): $R^1-CO-O-[C_mH_nO_x]_y-O-R^2$ wherein $R_1$ is a saturated or non-saturated $C_1$-$C_{30}$ alkyl, $R_2$ is a sterol moiety, m=5-7, n=9-14 and x=5-7, y=1-5. The present invention relates further to a method of for hydrolysing steryl gylcosides using said enzymes in biofuel, oil and/or fat.

17 Claims, 3 Drawing Sheets

ENZYMATIC HYDROLYSIS OF ACYLATED STERYL GLYCOSIDES AND METHOD FOR TREATING BIOFUEL

CROSS-REFERENCE TO RELATED APPLICATIONS

This application is the United States national phase of International Application No. PCT/EP2014/067336 filed Aug. 13, 2014, and claims priority to European Patent Application No. 13004067.8 filed Aug. 16, 2013, the disclosures of which are hereby incorporated in their entirety by reference.

BACKGROUND OF THE INVENTION

Field of the Invention

The present invention relates to a method of hydrolyzing using at least one glycosidase, a method for treating biofuel, and biofuel obtained by this method.

Description of Related Art

The use of renewable biofuel has increased rapidly over the last decades, in particular in view of the problematic of global warming. Typical renewable resources for biofuel are vegetable oils such as rape seed oil, soy oil and other oils.

Biofuel, and here in particular biodiesel, is produced from crude vegetable oil such as rape seed oil, soy bean oil or Jatropha oil by a degumming step, in which phospholipids are removed from the oil either chemically or enzymatically followed by a transesterification step, wherein the triacylglycerols contained in the vegetable oil are reacted with methanol and undergo thereby a transesterification step for producing glycerol and fatty acid methyl esters. Subsequently, the glycerol is removed and the fatty acid methyl esters form the biodiesel which can replace the mineral oils typically used.

Vegetable oils usually contain the phytochemicals acylated steryl glycosides (ASG) and steryl glycosides (SG), whereby the latter ones are not soluble in fatty acid alkyl esters (biodiesel). Steryl glycosides precipitate and may result in a filter clogging and/or causing an engine fueled by the biofuel to stop. Acylated steryl glycosides are transformed into the poorly soluble steryl glycosides during the transesterification step of the biodiesel production process. This in turn leads to an increase of the amount of insoluble and precipitated steryl glycosides and the problems associated therewith.

The steryl glycoside may precipitate during storage over the course of several weeks. Thus, although freshly produced biodiesel may meet the quality standards, after some weeks of storage the biodiesel may no longer pass the filter test and can thus not any longer be used.

Several approaches have been applied in the past for solving the problem of steryl glycosides precipitation during the biodiesel production. One approach is the application of an additional filtration step and/or centrifugation steps. The disadvantages of removing steryl glycosides by filtration or centrifugation are in particular the relative high costs associated therewith and the time required.

Further alternative approaches for removing steryl glycosides comprise the application of enzymes for hydrolyzing the steryl glycosides. EP 2098585 A1 (WO 2009/106360 A2) applies enzymatic hydrolysis for removing steryl glycosides by converting said steryl glycosides into more soluble free sterols and sugars. The enzymes suggested to be used are amongst others acylases, transesterases, transferases or hydrolases such as glycosidases, in particular beta-glucosidases, beta-glucanases, chitinases and cellulases.

A similar approach for removing steryl glycosides is reported in WO 2010/004423 A2 wherein glycosidases, glucosidases or amyloglucosidases are used for hydrolyzing the glycosidic bond in steryl glucosides such that the amount of steryl glucosides is reduced in oil, fat or biofuel.

WO 2010/102952 A1 describes a further alternative approach for removing steryl glycosides in fatty acid alkyl esters wherein the steryl glycosides are enzymatically acylated after transesterification resulting in acylated steryl glycosides, which do not precipitate in fatty acid alkyl esters (biodiesel). The enzymes used are mainly lipases or are preferably lipases or acyltransferases.

The methods applied for removing steryl glycosides, in particular the methods for enzymatic conversion of steryl glycosides, are focusing on processes after the transesterification process in the course of biodiesel production. Furthermore, said methods deal with the hydrolysis and conversion of steryl glycosides only.

As previously mentioned acylated steryl glycosides (ASG) are converted during the transesterification step in the biofuel production into steryl glycosides (i.e. without the fatty acid moiety), which are insoluble in biodiesel leading to precipitation resulting in filter plugging. As mentioned, the present methods focus on the enzymatic hydrolysis of acylated steryl glycosides. So far, no method or enzyme has been reported which is able to directly degrade or hydrolyze acylated steryl glycosides.

SUMMARY OF THE INVENTION

The present invention thus aims to overcome the problem related to the presence of acylated steryl glycosides, in particular in the process of biodiesel production.

Accordingly, at least one glycosidase of the class EC 3.2.1.21, EC 3.2.1.4, EC 3.2.1.7 and/or EC 3.2.1.80 for hydrolyzing at least one glycoside bond in at least one substrate selected from the group of acylated steryl glycosides of the general formula I, $$R^1\text{—CO—O—}[C_mH_nO_x]_y\text{—O—}R^2 \quad (I)$$

wherein
$R^1$ is a saturated or non-saturated $C_1$-$C_{30}$ alkyl,
$R^2$ is a steryl moiety,
m=5-7, n=9-14 and x=5-7,
y=1-5
is provided.

The present invention thus provides an approach for enzymatic hydrolysis of acylated steryl glycosides wherein said acylated steryl glycosides undergo hydrolysis to free sterols, which are soluble in biodiesel, and sugars and fatty acids which can be removed into a polar phase, for instance by using polar solvents.

It is the first time that enzymes have been reported which are able to cleave the glycosidic bond in acylated steryl glycosides. The same enzyme preparations, in particular inulinase preparations, are also able to hydrolyze the non-acylated steryl glycosides converting these conjugates into a state that will not result in solubility problems at a later stage of the biodiesel process. The present enzyme preparations, in particular the inulinase preparations, are highly efficient in water-based systems meaning that up to 100% of the present acylated steryl glycosides and steryl glycosides can be transformed into free sterols, sugars, fatty acids and/or their esters. Once this procedure is applied on crude vegetable oils, the content of glycosylated sterols can be efficiently decreased before the transesterification process that produces the biodiesel.

The used enzymes are surprisingly able to accept the much more bulky acylated steryl glycosides. In contrast, it has been commonly accepted that the bulky acyl group has to be cleaved before a hydrolysis of the glycosidic bond may occur. In the past the removal of the acyl group was reported using different esterases or lipases. This approach however is not favorable since esterases and lipases also hydrolyze the triacylglycerol present in the vegetable oils leading to a significant increase in free fatty acids what in turn represents a negative quality indicator in biodiesel. The presently used enzymes are however able to hydrolyze the glycosidic bond in acylated steryl glycosides as well as in steryl glycosides in crude oils before transesterification and thus inhibit the precipitation of steryl glycosides and the associated difficulties in later stages of the process.

In an embodiment the at least one glycosidase can be a β-glucosidase (EC 3.2.1.21), a cellulase or hemicellulase (EC 3.2.1.4), an endo-inulinase (EC 3.2.1.7), a fructane beta-fructosidase (EC 3.2.1.80) or a mixture thereof.

It is in particular preferred that the at least one glycosidase of the class 3.2.1.7 is an endoinulinase typically catalyzing the endohydrolysis of (2->1)-beta-D-fructosidic linkages in inulin. The endoinulinase may be selected from a group of organism comprising *Aspergillus* sp., preferably *Aspergillus niger*, *Aspergillus ficuum* or *Aspergillus fumigatus*, *Xanthomonas* sp., preferably *Xanthomonas oryzae*, *Penicillium* sp., preferably *Penicillium* sp. TN-88 and *Penicillium purpurogenum*, *Bacillus* sp., preferably *Bacillus smithii*, *Arthrobacter* sp., preferably *Arthrobacter* sp. S37, *Kluyveromyces* sp., preferably *Kluyveromyces marxianus*, *Pseudomonas* sp., preferably *Pseudomonas mucidolens*, *Geomyces* sp., preferably *Geomyces pannorum*, *Meyerozyma* sp., preferably, *Meyerozyma guilliermondii*, *Streptomyces* sp., preferably *Streptomyces griseus*.

The at least one glycosidase of the class EC 3.2.1.80 is an exoinulinase selected from a group of organism comprising *Aspergillus* sp., preferably *Aspergillus niger*, *Aspergillus ficuum*, *Aspergillus awamori* or *Aspergillus fumigatus*, *Kluyveromyces* sp., preferably *Kluyveromyces marxianus*, *Arabidopsis thaliana*, *Triticum* sp., preferably *Triticum aestivum*, *Cichorium* sp., preferably *Cichorium intybus*, *Cryptococcus* sp., preferably *Cryptococcus aureus*, *Penicillium* sp., preferably *Penicillium* sp. TN-88 and *Penicillium purpurogenum*, *Actinomyces* sp., preferably *Actinomyces naeslundii*; *Streptomyces* sp., *Lactobacilus* sp., preferably *Lactobacillus pentosus*, *Bacillus* sp., preferably *Bacillus subtilis*, *Streptococcus* sp., preferably *Streptococcus salvarius* and others.

It is to be understood that also modified enzymes, i.e. enzymes modified in their primary and/or secondary structure or glycosylation pattern, may be used as long as their catalytic activity regarding the ASG substrates is maintained.

In one embodiment, an inulinase enzyme used may be an enzyme preparation consisting of exoinulinase (EC 3.2.1.80) and endoinulinase (3.2.1.7) from *Aspergillus niger*. It is also possible to apply an enzyme preparation consisting of endoinulinase (3.2.1.7) from *Aspergillus niger* only. In an alternative, lyophilized inulinase from *Aspergillus niger* being a mixture of exoinulinase and endoinulinase can be used.

In an embodiment of the present invention the moiety $R^1$ is a saturated or non-saturated $C_5$-$C_{26}$ alkyl preferably a $C_6$-$C_{20}$ alkyl. Thus, $R^1$ may be a saturated or non-saturated alkyl moiety typically found in fatty acids. $R^1$ may be in particular a $C_{15}$ alkyl, $C_{17}$ alkyl, $C_{17}$ with one, two or three double bonds, in particular cis-double bonds. $R^1$ can be for instance an alkyl moiety derived from palmitic acid, stearic acid, oleic acid, linoleic or linolenic acid.

In a further embodiment the moiety $R^2$ is selected from a group comprising of, but not limited to sitosterol, campesterol, stigmasterol, brassicasterol, stigmastadienol, dihydrositosterol, sitostanol and d5-avenasterol. In general any possible sterol moiety is conceivable as R2.

The sugar moiety $—[C_mH_nO_x]_y—O—$ can be a monosaccharide (y=1) or a disaccharide (y=2). The monosaccharide may be glucose, mannose, xylose, fructose, myoinositol, galactose, arabinose or glucuronic acid, wherein glucose is preferred. The disaccharide may comprise beta-D-glucopyranosyl (1->6)-beta-D-glucopyranoside or myoinositol (1->6)-beta-D-glucopyranoside.

In case glucose is used as the sugar moiety the acylated steryl glycoside of the general formula I can have the following general structure:

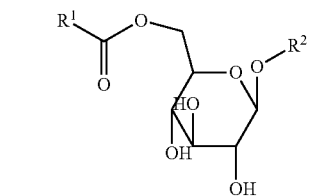

The acylated steryl glycosides may be selected from the group of palmitic, stearic, oleic, linoleic or linolenic acid esters of sitosterol, campesterol, or stigmasterol glucosides and galactosides.

A typical example of an acylated steryl glycoside is for instance sitosteryl palmitoyl glycoside having the following structure:

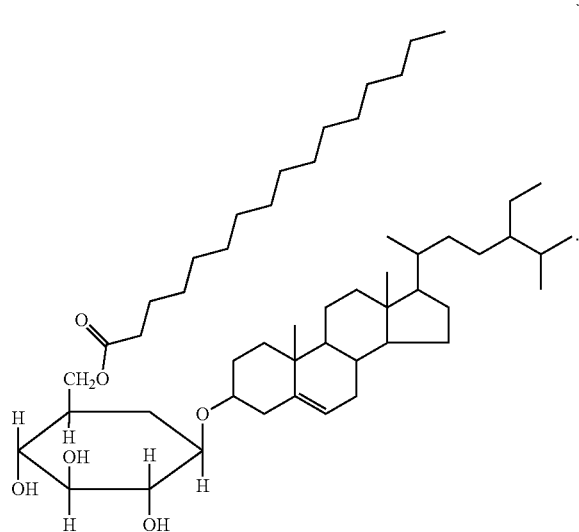

When applying a glycosidase preparation of the present invention, in particular, an inulinase preparation, the glycosidic bond is hydrolyzed as depicted in the following equation:

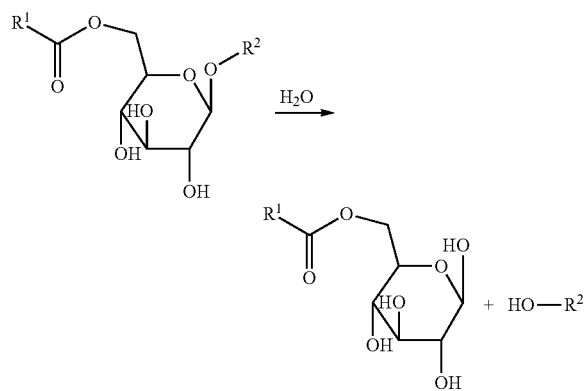

The present enzyme preparations for hydrolyzing acylated steryl glycosidases or a mixture of acylated steryl glycosidases and steryl glycosidases is used in an aqueous buffer system at a pH between 3 to 8, preferably between 4 and 7, most preferably between 5 and 6 and at a temperature between 20 to 100° C., most preferably between 30 to 55° C. The aqueous buffer system can be any buffer system being able to maintain the above-mentioned pH value. However, 0.1 molar sodium acetate buffer is the most preferred aqueous buffer system in the present case.

Furthermore, suitable dispersants or detergents can be added such as water-miscible solvents, most preferably ethanol and DMSO or detergents such as Triton-X, taurocholate etc. The incubation time is between 0.5 and 100 hours, most preferably between 15 and 25 hours.

As mentioned above, the enzyme preparations, such as the inulinase preparations, can be used in a method for hydrolyzing at least one acylated steryl glycoside and/or at least one steryl glycoside in biofuel, oil and/or fat by mixing said enzyme or enzyme preparations with the biofuel, oil or fat.

The biofuel, oil and/or fat are vegetable oils or vegetable fats comprising acylated and non-acylated steryl glycosides.

In an embodiment the oil, fat or biofuel to be treated may a vegetable oil selected from the group consisting of rapeseed oil, canola oil, soy bean oil, Jatropha oil, rice bran oil, palm oil, corn oil, cotton seed oil, sunflower oil, safflower oil, mustard seed oil, olive oil, peanut oil, castor oil, palm kernel oil, coconut oil, lupine oil, flaxseed oil, evening prime rose oil, jojoba oil, sheanut oil or camelina oil. In a most preferred embodiment the oil, fat or biofuel may be a vegetable oil selected from the group consisting of rapeseed oil, soy bean oil, corn oil, sunflower oil, rice bran oil or palm oil.

The present method may comprise a degumming step, preferably an enzymatic degumming step. During the degumming step phospholipids contained in the vegetable oil are separated and removed. Such a degumming step may be typically carried out by mixing hot water with warm crude oil. During this water degumming step, the phosphatides and other gums, which become insoluble in the oil when hydrated are removed by subsequent filtration or centrifugation.

Suitably the hydrolysis of acylated and non-acylated steryl glycosides can take place before, during or after the degumming step. However, a hydrolysis and thus removal of the steryl glycosides is preferably carried out during the degumming step. In other words, the admixing of the enzymatic preparation, such as inulinase preparation with a vegetable oil occurs preferably during the water degumming and/or enzymatic degumming step.

In a further embodiment the present method comprises at least one transesterification step, preferably an enzymatic transesterification step, following the degumming step. During this transesterification process triacylglycerols present in the vegetable oils are hydrolyzed in the presence of methanol to glycerol and fatty acid methyl ester. The fatty acid methyl esters (FAME) make up the biodiesel.

It is preferred that the hydrolysis of the at least one acylated steryl glycosides and/or the at least one steryl glycosides takes place before said transesterification step. Thus, it is conceivable and possible to add the present enzyme preparations such as inulinase preparations also to the vegetable oil or fat during or after the degumming step and before the enzymatic transesterification process.

It is furthermore possible to add the present enzymatic preparations such as inulinase preparation more than one time during the method described. Thus, the present enzyme preparations such as inulinase preparation may be added during the degumming step, in particular enzymatic degumming step, as well additionally before or even during the transesterification process.

Following the hydrolysis of the acylated and non-acylated steryl glycosides the sugars and fatty acids as hydrolysis product are removed by means of a polar phase such as a polar solvent. The sterols which are cleaved during the hydrolysis process do not have to be removed since they are soluble in the fatty acid methyl ester and do not negatively influence the properties of the biodiesel.

If however, the processed vegetable oil is to be used in the food industry, then the soluble sterols may be removed by known methods.

The oil, fat or biofuel obtainable by the just described method using glycosidase preparations for hydrolyzing the glycosidic bonds in an acylated steryl glycoside and/or non-acylated steryl glycoside to a free sterol, sugar, acylated sugar or fatty acid is preferably free of any steryl glycosides. This means, that the oil, fat or biofuel obtained comprises less than 10% steryl glycosides, in particular less than 5% steryl glycosides.

The present method provides a simple and cost efficient method for removing acylated and non-acylated steryl glycosides from vegetable oils, which are to be used as biofuel substrates or in the food industry. One advantage of the present invention is the removal of steryl glycosides from the vegetable oils or fat or from the biofuel before the steryl glycoside precipitates. The conditions used by the present method result in a complete conversion of acylated and non-acylated steryl glycosides into free sterols. When applied at early stages of the biodiesel process glycosylated sterols can be hydrolyzed and removed before the transesterification process.

BRIEF DESCRIPTION OF THE DRAWINGS

The present invention is explained in the following in more detail by means of several examples with reference to the Figures. It shows.

DETAILED DESCRIPTION OF THE INVENTION

Figure 1:
FIG. 1 a first scheme showing the hydrolyzing process catalyzed by a glycosidase according to a first embodiment, FIG. 2 a GC-FID chromatogram of the free sterols enzymatically hydrolyzed from ASG samples, FIG. 3 a diagram showing the amount of free sterols after incubation with inulinase preparations, FIG. 4 a diagram quantifying the remaining amount of ASG after incubation with inulinase preparations, FIG. 5 a further diagram quantifying the amount of free sterols after incubation of a SG from soy lecithin with different inulinase preparations, FIG. 6 a further scheme showing the main stages of biodiesel production process according to an embodiment of the present method.

FIG. 1 illustrates the chemical reactions taking place when treating a mixture of ASG and SG with an inulinase preparation. The enzyme hydrolyses the glycosidic bond in ASG and SG without hydrolysing the acyl chain. The hydrolysation using inulinase results in the formation of free sterols which are soluble. The released sugar and sugar fatty acid esters (acyl-sugar) are soluble in the polar phase of crude oil processing.

Figure 6:
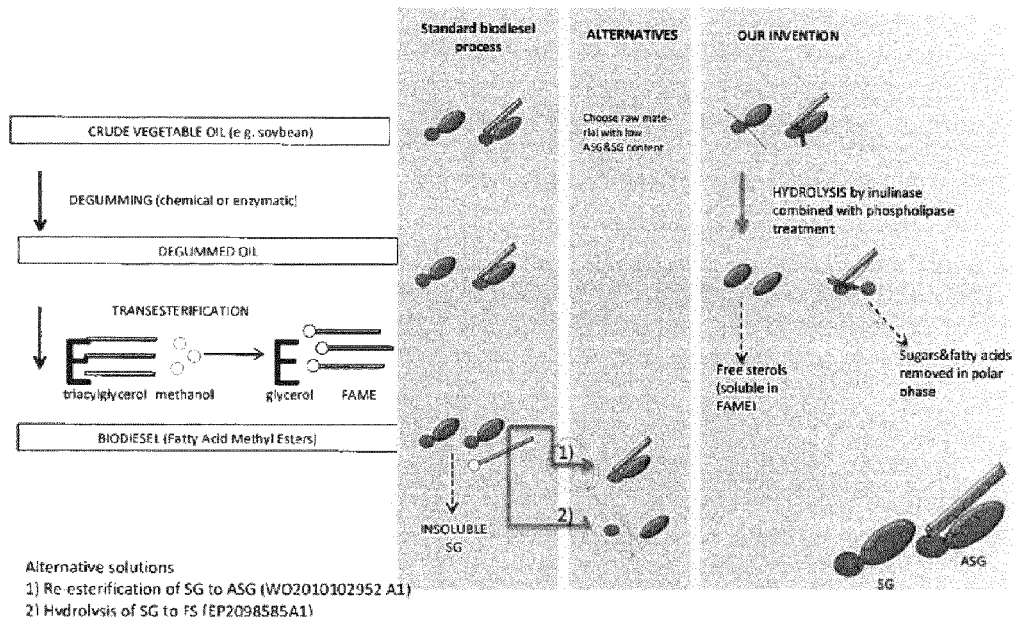

FIG. 6 illustrates the main stages of biodiesel production process and the state of ASG and SG in each of the singular stages. According to the embodiment shown in FIG. 6 the hydrolysis of ASG and SG by inulinases is combined with the degumming step (phospholipase treatment). The inulinase treatment is thus effected before the transesterification step.

EXAMPLE 1

The following enzyme preparations were used:
Fructozyme® L: commercial enzyme preparation (liquid) consisting of exoinulinase (3.2.1.80) and endoinulinase (3.2.1.7) from *Aspergillus niger*, from Novozymes Denmark;
Novozym® 960: commercial enzyme preparation (liquid) consisting of endoinulinase (3.2.1.7) from *Aspergillus niger*, from Novozymes Denmark; and
Lyophilized inulinase from *Aspergillus niger* (mixture of exo- and endoinulinase), from Sigma-Aldrich Switzerland.

a) Hydrolysis of Commercially Available ASG

A stock solution of pure ASG in hexane:isopropanom 85:15 (purity: 98+%, Matreya, US) was prepared and used for further experiments. Correct volume was added to 30 ml tube in order to have an initial amount of 200 µg ASG. Solvent was evaporated and ASG were redissolved in 500 µl ethanol. Further, 0.1 M sodium acetate buffer pH 4.5 was added followed by the addition of the enzyme (total volume of buffer and enzyme=3 ml). The incubation was carried out at 40° C. for 21 hours in a shaking device with controlled temperature. Hydrolysis was stopped by starting the extraction of ASG using the Bligh and Dyer method. Prior to extraction, 2 ml of internal standard solution (0.008 mg DHC /ml EtOH) was added. The lower phase was then collected and evaporated to dryness, redissolved in 2 ml EtOH and transferred to a fresh tube. For GC analysis of the free sterols released in the enzymatic reaction (procedure as in Nyström, Schär, & Lampi, 2012, European Journal Lipid Science and Technology, 114 (6), 656-669), 1 ml was withdrawn, dried and derivatised to TMS-derivatives. For HPLC of the possibly remaining intact substrates, the remaining ethanol solution was dried and redissolved in hexane:isopropanol 85:15 and analysed using hexane:isopropanol 85:15 as mobile phase (column: Luna HILIC from Phenomenex). Samples were analysed in duplicate.

b) Hydrolysis of ASG in Samples Extracted from Soy Beans and Soy Lecithin

Total lipid extraction of soy beans and soy lecithin (both 2 g) was done by accelerated solvent extraction (ASE). Lipids were further fractionated using solid phase extraction whereas the ASG fraction was collected, evaporated to dryness. ASG fraction from soybeans was redissolved in 500 µl EtOH, fraction from lecithin was redissolved in 1.5 ml EtOH and devided into three 500 µl volumes. Samples were then subjected to enzymatic hydrolysis as described above (soy bean: 1 sample, only 200 µl Novozyme 960 added, lecithin: 2 samples, 200 µl Novozyme 960 and 200 µl Fructozyme L tested) and measured by GC and HPLC also described above.

c) Samples with Commercial ASG

Free sterols stigmasterol, campesterol, stigmasta-5,23-dienol, sitosterol, sitostanol and d5-avenasterol (see FIG. 2) were detected in all the samples incubated with either Novozym 960, Fructozyme L or lyophilized inulinase. Samples without enzyme (blank) only showed a peak for the internal standard (DHC), which was added prior to extraction. Therefore, all the inulinase preparations were able to effectively hydrolyse ASG into free sterols. Due to the absence of free sterols in the blank samples other hydrolysis pathways (eg acid hydrolysis) causing the breakdown of ASG can be excluded.

Figure 2:
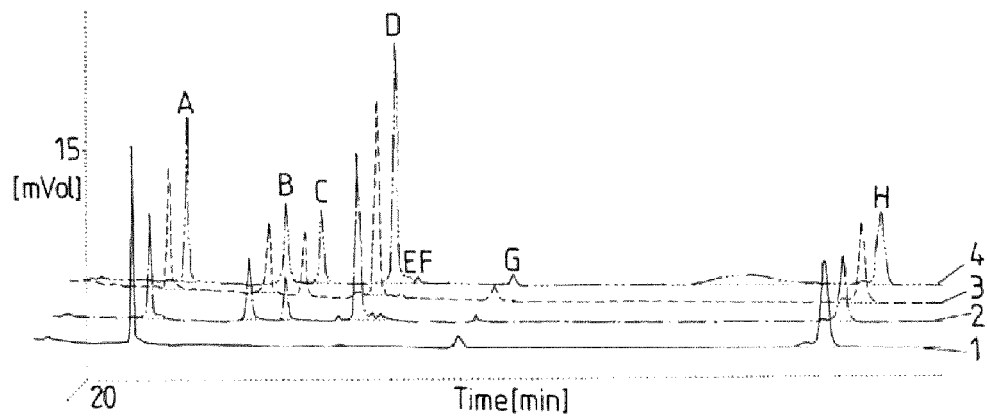

FIG. 2 shows a 3D-overlay of GC-FIC chromtograms of enzymatically hydrolysed ASG samples; 1: blank (no enzyme added), 2: ASG+Fructozyme L, 3: ASG+Novozyme 960, 4: ASG+lyophilized inulinase; peak identification: A: DHC (internal standard), B: Campesterol, C: Stigmasterol, D: Sitosterol, E: Sitostanol, F: Δ5-avenasterol, G: unknown peak (no sterol), H: unknown peak (no sterol)

Figure 3:
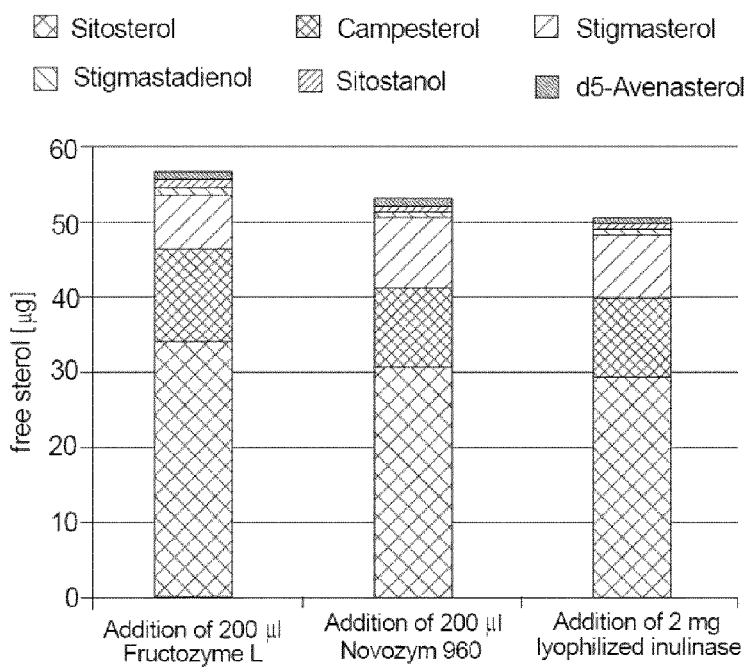

Quantification based on internal standard showed that the total amount of free sterols was at similar levels for all inulinase preparation tested (FIG. 3). In case 200 µg ASG (initial amount) are fully hydrolysed 100.6 pg free sterols should be released using a conversion factor of 0.503. Incubation with Fructozyme L resulted in 57.1 µg free sterols representing 113.5 µg hydrolysed ASG, with Novozym 960 in 53.6 µg free sterols representing 106.5 µg hydrolysed ASG and with lyopihilzed inulinase in 50.8 µg free sterols representing 101.0 µg hydrolysed ASG. Therefore, ASG (initially 200 µg) were decreased by 56.8% using Fructozyme L, by 53.6% using Novozym 960 and by 50.8% using lyophilized inulinase. Higher percentage of decrease can be achieved by adapting the condition parameters with regards to amount of enzyme, pH, temperature and dispersant added as it was obtained within SG hydrolysis with inulinase (almost 100%).

Figure 4:
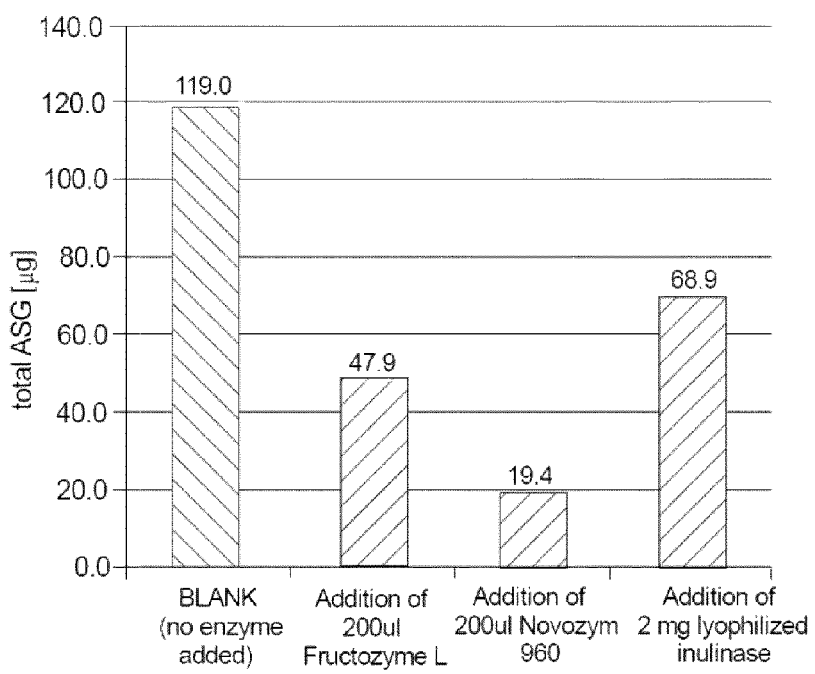

The HPLC results (FIG. 4) also demonstrated that ASG are not yet fully hydrolysed. However, compared to the blank sample the ASG amount could be reduced by 59.8% with Fructozyme L, by 83.7% with Novozym 960 and by 42.1% with lyophilized inulinase.

d) Samples with ASG Extracted from Soy Beans and Soy Lecithin

The incubation ASG fraction extracted from soy beans and soy lecithin with Novozyme 960 (and additionally Fructozyme L for lecithin) also resulted in free sterols demonstrating the potential of inulinases to hydrolyse ASG in more complex system (containing traces of contaminants coming from raw material). The same free sterol pattern was observed as with the pure ASG samples sitosterol, campesterol, stigmasterol, stigmasta-5-23-dienol, sitostanol, d5-avenasterol.

Figure 5:
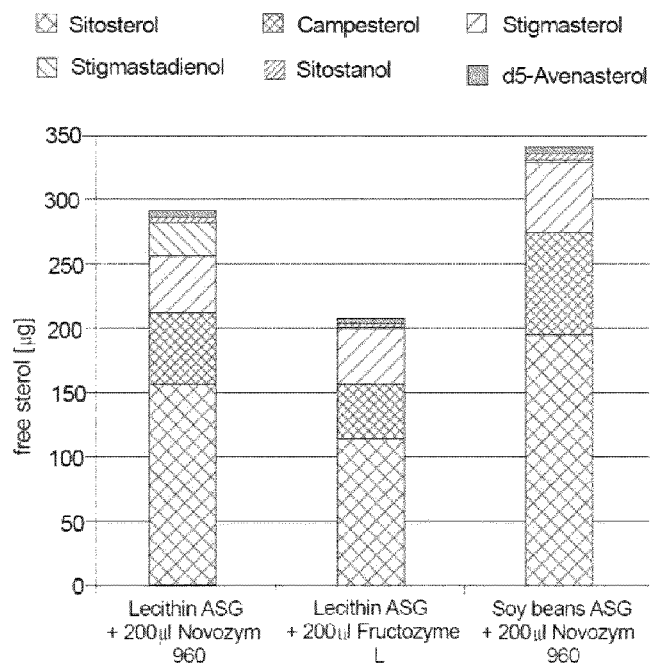

As shown in FIG. 5, the addition of 200 µl Novozym 960 to lecithin ASG resulted in 291.1 µg free sterols (=579.4 µg hydrolysed ASG) whereas with 200 µl Fructozyme L 209.1 µg free sterols were obtained (=415.6 µg hydrolysed ASG). The incubation of soy bean ASG with 200 µl Novozym 960 released 343.8 ug free sterols (=683.5 µg hydrolysed ASG). In the lecithin sample with Novozym 960, 19.1 µg of remaining ASG were quantified whereas in the one with Fructozyme L 11.0 µg ASG were found. In the soy bean sample, 135.1 µg ASG remained intact.

e) Conclusion

ASG either as pure mixture or extracted from soy beans or soy lecithin were subjected to enzymatic hydrolysis in a water-based system with three different commercial inulinase preparations. The products of the hydrolysis, free sterols, were detected in all of the incubated samples demonstrating the capability of inulinases to cleave the glycosidic bond in ASG.

The invention claimed is:

1. A method for hydrolyzing at least one glycoside bond in at least one substrate selected from the group of acylated steryl glycosides of the general formula I $R^1\text{—}CO\text{—}O\text{—}[C_mH_nO_x]_y\text{—}O\text{—}R^2$ wherein $R_1$ is a saturated or non-saturated $C_1$-$C_{30}$ alkyl,
$R_2$ is a sterol moiety,
m=5-7, n=9-14 and x=5-7,
y=1-5
using at least one glycosidase of the class EC 3.2.1.7 and/or EC 3.2.1.80.

2. The method according to claim 1, wherein at least one glycosidase of the class EC 3.2.1.7 is an endoinulinase derived from an organism, wherein the organism is selected from the group consisting of *Aspergillus* sp., *Xanthomonas* sp., *Penicillium* sp., *Bacillus* sp., *Arthrobacter* sp., *Kluyveromyces* sp., *Pseudomonas* sp., *Geomyces* sp., *Meyerozyma* sp., and *Streptomyces* sp.

3. The method according to claim 1, wherein at least one glycosidase of the class EC 3.2.1.80 is an exoinulinase derived from an organism, wherein the organism is selected from the group consisting of *Aspergillus* sp., *Kluyveromyces* sp., *Arabidopsis thaliana*, *Triticum* sp., *Cichorium* sp., *Cryptococcus* sp., *Penicillium* sp., *Actinomyces* sp., *Streptomyces* sp., *Lactobacilus* sp., *Bacillus* sp., *Streptococcus* sp., and others.

4. The method according to claim 1, wherein $R^1$ is a saturated or non-saturated $C_5$-$C_{26}$ alkyl.

5. The method according to claim 1, wherein $R^2$ is selected from a group consisting of sitosterol, campesterol, stigmasterol, brassicasterol, stigmastadienol, dihydrositosterol, sitostanol and d5-avenasterol.

6. The method according to claim 1, wherein —$[C_mH_nO_x]_y$—O— is a sugar moiety selected from a group consisting of a glucose, galactose, glucuronic acid, mannose, xylose or arabinose.

7. The method according to claim 1, wherein the substrate is a mixture of different acylated steryl glycosides or a mixture of acylated steryl glycosides and steryl glycosides.

8. A method for hydrolyzing at least one acylated steryl glycoside and/or at least one steryl glycoside in biofuel, oil and/or fat by mixing at least one glycosidase of the class EC 3.2.1.7 and/or EC 3.2.1.80 with the biofuel, oil or fat.

9. The method according to claim 8, comprising a degumming step.

10. The method according to claim 9, wherein the hydrolysis of at least one acylated steryl glycoside and/or at least one steryl glycoside takes place before, during or after the degumming step.

11. The method according to claim 8, comprising at least one transesterification step.

12. The method according to claim 11, wherein the hydrolysis of the at least one acylated steryl glycosides and/or the at least one steryl glycosides takes place before the transesterification.

13. The method according to claim 8, wherein following the hydrolysis of the at least one acylated steryl glycosides and/or the at least one steryl glycosides the sugars and fatty acids are removed by means of a polar phase.

14. The method according to claim 4, wherein $R^1$ is a saturated or non-saturated $C_6$-$C_{20}$ alkyl.

15. The method according to claim 6, wherein —$[C_mH_nO_x]_y$—O— is a glucose sugar moiety.

16. The method according to claim 9, wherein the degumming step is an enzymatic degumming step.

17. The method according to claim 11, wherein the transesterification step is an enzymatic transesterification step.

* * * * *

UNITED STATES PATENT AND TRADEMARK OFFICE
CERTIFICATE OF CORRECTION

| | | |
|---|---|---|
| PATENT NO. | : 9,957,453 B2 | Page 1 of 1 |
| APPLICATION NO. | : 14/912127 | |
| DATED | : May 1, 2018 | |
| INVENTOR(S) | : Linda Munger et al. | |

It is certified that error appears in the above-identified patent and that said Letters Patent is hereby corrected as shown below:

In the Claims

Column 9, Line 26, Claim 1, delete "$R_1$is" and insert -- $R_1$ is --

Column 9, Line 27, Claim 1, delete "$R_2$is" and insert -- $R_2$ is --

Column 9, Lines 43-44, Claim 3, delete "Cryptococcussp.," and insert -- Cryptococcus sp., --

Signed and Sealed this
Seventh Day of August, 2018

Andrei Iancu
*Director of the United States Patent and Trademark Office*